United States Patent [19]

Betz et al.

[11] Patent Number: 4,759,349
[45] Date of Patent: Jul. 26, 1988

[54] SURGICAL INSTRUMENT HAVING A HEAT SINK FOR IRRIGATION, ASPIRATION, AND ILLUMINATION

[75] Inventors: Bard B. Betz, Reno, Nev.; Daniel J. Conley, Oceanside, Calif.; Larry Blankenship, Boulder, Colo.; Stephen J. Krienick, San Diego; Bradley J. Denny, San Marcos; Charles T. Bovey, Escondido; Jeffrey P. Castleberry, San Diego, all of Calif.

[73] Assignee: Vitalmetrics, Inc., San Diego, Calif.

[21] Appl. No.: 832,478

[22] Filed: Feb. 24, 1986

[51] Int. Cl.⁴ .................. A61B 1/06; A61M 1/00
[52] U.S. Cl. ............................ 128/6; 604/27; 604/39; 604/902
[58] Field of Search ........................ 128/4–6, 128/7, 8, 9, 11, 13, 16, 18, 22, 23; 433/29, 80; 604/19–22, 27–36, 39, 43, 48, 73, 131, 902

[56] References Cited

U.S. PATENT DOCUMENTS

| | | | |
|---|---|---|---|
| 3,191,600 | 6/1965 | Everett | 604/902 |
| 3,371,202 | 2/1968 | Moore et al. | 128/23 UX |
| 3,498,286 | 3/1970 | Polanyi et al. | 604/21 |
| 4,330,274 | 5/1982 | Friedman et al. | 433/29 |
| 4,398,885 | 8/1983 | Logé et al. | 433/29 |
| 4,400,168 | 8/1983 | Buechel et al. | 604/48 |
| 4,617,013 | 10/1986 | Betz | 604/904 |

Primary Examiner—C. Fred Rosenbaum
Assistant Examiner—J. L. Kruter
Attorney, Agent, or Firm—Freilich, Hornbaker, Rosen & Fernandez

[57] ABSTRACT

A surgical instrument and support unit for enabling a user using one hand to probe an incision and illuminate, irrigate, and aspirate the incision. The surgical instrument has a probe with illumination, irrigation, and aspiration ports on the end. The probe is coupled to a handle having controls for the irrigation and aspiration functions. Light from a high intensity lamp in the handle is transmitted through an optical fiber to the illumination port. A heat sink enclosing the lamp draws heat away from the lamp and transfers the heat to the aspirated fluid passing through the heat sink. The support unit is controlled by a microcomputer and provides an electrical supply for the lamp and a pressurized fluid supply for irrigation. The sources of the irrigation fluid is a standard hospital flexible bag. A bladder inflated by an air pump pressurizes the flexible bag. The pump is also utilized to deflate the bladder to allow rapid changing of the flexible bag during a surgical procedure.

23 Claims, 6 Drawing Sheets

SURGICAL INSTRUMENT HAVING A HEAT SINK FOR IRRIGATION, ASPIRATION, AND ILLUMINATION

BACKGROUND OF THE INVENTION

1. Field of the Invention

The present invention pertains to the surgical instrument art, and more particularly, to a surgical instrument and support unit for providing irrigation, aspiration, and illumination in a surgical incision.

2. Background Art

In many surgical procedures it is important and difficult to provide adequate lighting at the surgical site. Customarily, surgical rooms have large overhead lights to provide the lighting. On occasion some surgeons or assistants may carry auxillary light of one type or another to attempt to improve lighting at the exact position of surgery. In this type of lighting, shadows are a problem due to interference with the light path by the persons performing the surgery and the instruments and equipment being used.

Another important function during many surgical procedures is the irrigation of the surgical area with various fluids. It has been customary to use hand-held syringes filled by a nurse or other surgical assistant from a bowl and to irrigate by squeezing the syringe bulb. This procedure has many problems including, among others, the necessity for a surgical assistant to spend much time filling the syringes, delay in irrigating when desired, and inaccurate pressure control.

Another important function during many surgical procedures is the removal of fluids and small particles by aspiration from the incision. This function is performed by an aspiration tube handled by a member of the surgical team and is extremely important in keeping all portions of the incision clean and visible. The various materials are drawn by suction into the tube and away from the surgical area by a vacuum through the aspiration tube.

A surgical instrument for performing these three functions is disclosed in U.S. patent application Ser. No. 689,511, filed Jan. 8, 1985, now U.S. Pat. No. 4,617,013 to John J. E. Betz entitled METHOD AND APPARATUS FOR SURGICAL IRRIGATION, ASPIRATION AND ILLUMINATION, assigned to Timron Instruments, Inc., a subsidiary of Vitalmetrics, Inc. The preferred embodiment disclosed therein comprises a hand-held instrument capable of simultaneously and cooperatively providing illumination, irrigation, and aspiration to the surgical site. The instrument includes a probe member and a handle member connected end-to-end and including three passageways for respectively supplying light, irrigating fluid, and suction to the surgical site.

SUMMARY OF THE INVENTION

The present invention is directed to an improved hand-held surgical instrument and support unit for the surgical instrument for irrigating and aspirating a surgical site and for delivering high intensity illumination to the site. More specifically, the present invention is directed to a surgical instrument constructed so as to accomodate a high intensity lamp (e.g. a halogen lamp capable of delivering on the order of 500–3000 foot candles of illumination) without transfering uncomfortable amounts of heat to the user's hand.

In accordance with one important aspect of the invention, the instrument incorporates a heat sink, e.g. a block of highly heat conductive material, to closely thermally couple the high intensity lamp to an aspiration passageway to thus enable the aspirating fluid to remove heat from the hand-held instrument.

In accordance with another aspect of the invention, the instrument incorporates a heat sensor for reducing the power supplied to the lamp when the monitored temperature exceeds a threshold level.

In accordance with a further aspect of the invention, the remote support unit is coupled to the hand-held instrument for supplying irrigating fluid and electrical power and control for the high intensity lamp.

In a preferred embodiment, the hand-held surgical instrument is preferrably fabricated to be disposable whereas the support unit is intended to be reused. The instrument includes a probe member used to actually probe a surgical site and provide light, irrigation, and aspiration thereto and a handle member that can be held in and operated by one hand to control the various functions. Irrigation and aspiration passageways extend through the handle and probe members opening at ports at the free end of the probe member. The handle member includes a lamp that receives electrical power from the support unit. The handle member also includes a finger operable valve coupled to the irrigation passageway for controlling the flow of an irrigation fluid supplied by the support unit and discharged from the irrigation port. The handle member also includes a heat sink closely thermally coupled to the lamp to draw heat away from the lamp. The heat sink includes an aspiration passageway for passing aspirated fluids therethrough to remove heat from and thus cool the heat sink.

One of the features of the preferred embodiment is a heat sink having a bleed hole passing between the atmosphere and the aspiration passageway to enable a user to readily control the flow of fluid into the aspiration port and providing additional surface area cooled by the air passing through the bleed hole to cool the heat sink. A heat sensing means such as a thermistor inside the handle is utilized by the support unit to measure the temperature of the handle and reduce the lamp current in case the temperature becomes too high. Since the aspiration fluid provides the primary means of cooling the heat sink, blockage of the aspiration port causes an increase in temperature. The support unit responds to the temperature rise by turning on a warning indicator.

One of the features of the preferred embodiment is an irrigation passageway having a compliant portion and an irrigation valve that normally collapses the compliant portion to stop the flow of irrigation fluid therethrough. When the compliant portion is not collapsed, the irrigation fluid flows out the irrigation port. The compliant portion passes through an aperture in a plunger in the valve. A biasing means moves the plunger in a first direction to collapse the compliant portion against the side of the aperture. When the plunger is moved in a second direction by pressing with a finger, the compliant portion opens allowing the irrigation fluid to pass through.

A reusable support unit cooperates with the surgical instrument. The preferred embodiment of the support unit includes a pressurizer for squeezing a flexible bag of irrigation fluid to cause the fluid to flow to the surgical instrument. The pressurizer preferably includes a chamber for holding the flexible bag and an inflatable bladder inside the chamber whereby inflation of the bladder presses the flexible bag against the chamber door creating pressure inside the flexible bag.

Another feature of the preferred embodiment is a pressurizer having a pump coupled to the bladder, a pressure transducer for producing a signal representing the pressure level in the bladder, and a microcomputer control means for controlling the pump according to the pressure level in the bladder. An accumulator is preferably coupled to the pump and the bladder and a bladder isolation valve is provided between the accumulator and the bladder. The pump is then able to pressurize the accumulator to a greater pressure than desired for the bladder. The pressure in the accumulator is then used to pressurize the bladder without operating the pump by bleeding air from the accumulator through the isolation valve to the bladder.

Another feature of the preferred embodiment is an evacuation means for deflating the bladder after an irrigation bag is empty allowing rapid changing of the bags. The evacuation means couples the vacuum side of the pump to the bladder.

Other features and advantages of the present invention will become apparent from the following detailed description, taken in conjunction with the accompanying drawings, which illustrate, by way of example, the principles of the invention.

DESCRIPTION OF THE PREFERRED EMBODIMENTS

Figures 1, 4A, 4B:
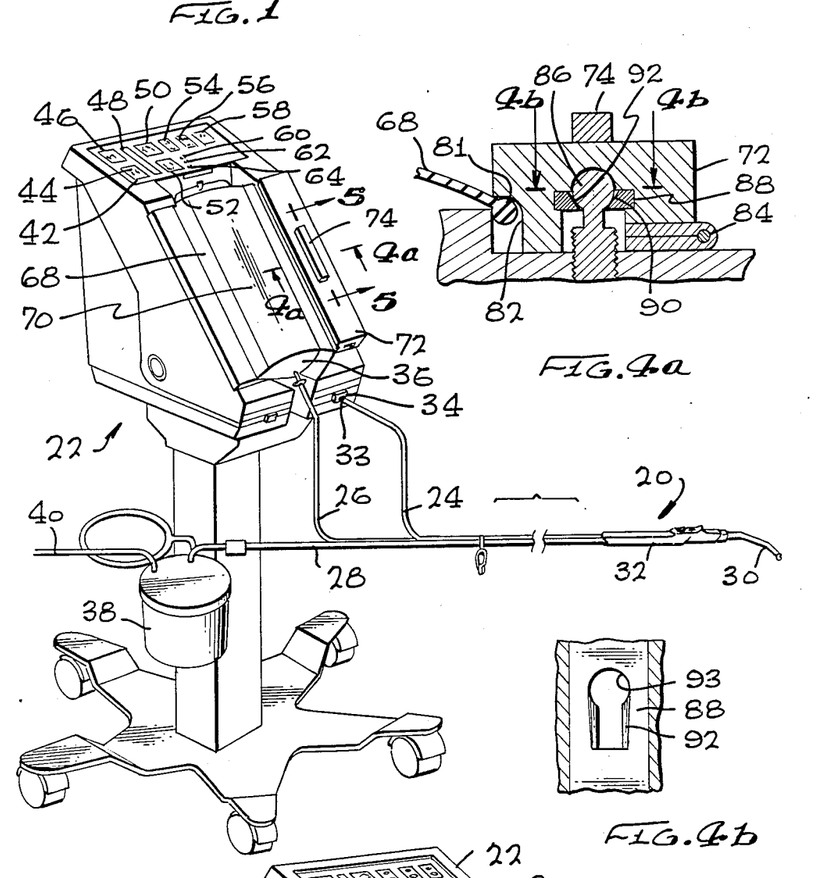
FIG. 1 is a perspective view of a surgical instrument and support unit of the present invention.
FIG. 4a is an enlarged sectional view along the line 4a—4a of FIG. 1 through the center of the door latch.
FIG. 4b is a top plan view of the sliding cam of FIG. 4a along the line 4b—4b.

Referring initially to FIG. 1, there is illustrated a perspective view of a surgical instrument, generally designated 20, coupled to a support unit, generally designated 22, in accordance with the present invention. The instrument 20 is preferrably designed to be relatively low cost and therefore disposable. The instrument 20 includes electrical wiring 24, an irrigation tube 26, and an aspiration tube 28 for connection to electrical, irrigation, and aspiration sources at the support unit 22. An elongated probe member 30 on an elongated handle member 32 is used for probing a surgical incision and has illumination, irrigation, and aspiration ports. Inside the handle member 32 is an electric lamp powered through the wiring 24 for creating light directed to emanate through an illumination port on the end of the probe member 30. An irrigation control means in the handle member 32 controls the flow of an irrigation fluid through the irrigation tube 26 to an irrigation port on the end of the probe member 30. A bleed hole in the handle member 32 is utilized to control the flow of fluid into an aspiration port at the end of the probe member 30 and out to the support unit 22 through the aspiration tube 28.

The surgical instrument 20 is connected to the support unit 22 by plugging a modular telephone type plug 33 into a wiring receptacle 34, the irrigation tube spike 35 into a standard hospital flexible bag 36 filled with irrigation fluid, and the aspiration tube suction connector 37 into a standard hospital suction collection container 38. The support unit 22 in turn receives electric power from the hospital electrical main to supply the lamp and support unit 22 requirements. The suction collection container 38 is connected to the hospital vacuum suction system through a suction connector tube 40.

Control of the overall operation of the surgical instrument 20 and the support unit 22 is by a control means that includes a microprocessor. A control panel 42 provides an interface between the operator and the microprocessor. The control panel 42 has an "irrigation off" switch 44, an "irrigation on" switch 46, a current and set point pressure bar graph 48, a "pressure increase" switch 50, a "pressure decrease" switch 52, a "lamp off" switch 54, a "lamp on low" switch 56, a "lamp on high" switch 58, a "lamp operating properly" indicator 60, an "aspiration blockage" indicator 62, and a "lamp defective" indicator 64.

One of the primary functions of the support unit 22 is to pressurize the flexible bag 36. A fluid supply means in the support unit 22 includes a chamber 66 for holding the flexible bag 36 and an inflatable bladder means 67 (FIG. 3) inside the chamber 66 underneath the bag 36. The chamber 66 provides a means for retaining the bag 36 in engagement with the bladder 67. A control means provides a means for inflating the bladder 67 to squeeze the bag 36. When the "irrigation on" switch 46 is switched on, the control means inflates the bladder 67 squeezing the bag 36 against the door 68 creating pressure inside that is transmitted through the irrigation tube 26 to the handle member 32.

The chamber 66 has a door 68 for inserting and removing the flexible bag 36 with a transparent portion 70 permitting viewing of the bag 36 inside the chamber 66 as the irrigation fluid is utilized during a surgical procedure. The door 68 includes a portion including the transparent portion 70 fabricated of a flexible material for bearing against and conforming to the bag 36. An interlocking door latch 72 provides a means for latching the door 68 against the side of the chamber 66 to retain the door 68 in position during pressurization. The latch 72 is locked in position by moving the latch handle 74 down.

Figure 2:
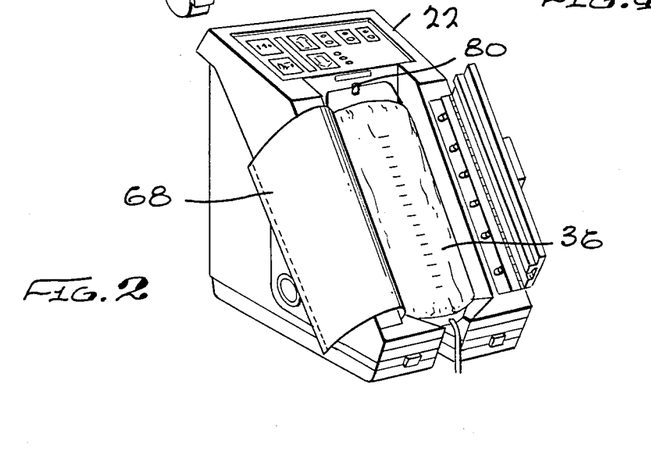
FIG. 2 is a perspective view of a portion of the support unit with the door open.

FIG. 2 is a perspective view of the support unit 22 with the door 68 open. The flexible bag 36 is exposed allowing a used bag to be removed and a new one inserted.

Figure 3:
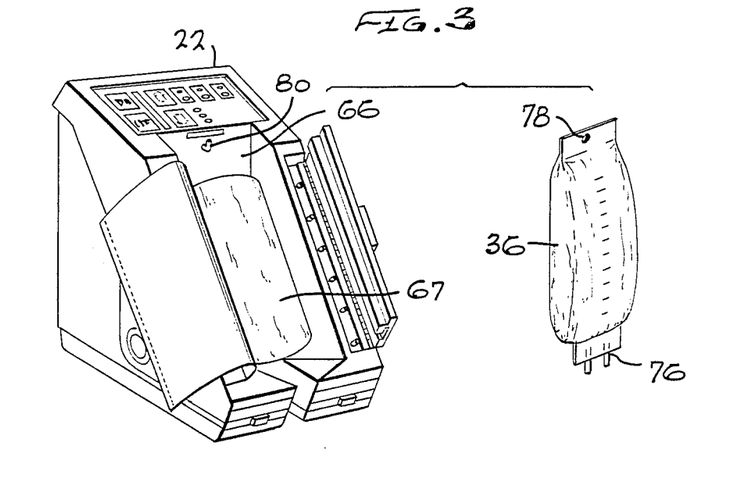
FIG. 3 is a perspective view of a portion of the support unit with the flexible irrigation bag removed.

FIG. 3 is a perspective view of a portion of the support unit 22 with the flexible irrigation bag 36 removed revealing the bladder 67. As shown in FIG. 3, the bag 36 is a new bag full of irrigation fluid. The irrigation tube 26 in FIGS. 1 and 2 is attached to the bag 36 through a connection point 76 outside the chamber 66. The bag 36 is then secured in the chamber 66 by placing the eye 78 of the bag 36 over the hook 80 as illustrated in FIG. 2. The door 68 is then placed over the bag 36 into the latch 72 and the latch secured by moving the latch handle 74 down as illustrated in FIG. 1. It will be appreciated that other types of compressible fluid reservoirs may be utilized for dispensing irrigation fluid other than the flexible bag 36 and that means other than the bladder 67 may be utilized for creating pressure against the fluid reservoir to squeeze the fluid therefrom.

FIG. 4a is an enlarged sectional view along the line 4a—4a of FIG. 1 through the center of the interlocking door latch 72. The edge of flexible door 68 is constructed with a rib 81 which is held in a recess 82 in the latch 72 that provides a means for selectively capturing and retaining the rib 81. The latch 72 is coupled to the chamber 66 on the opposite side by a hinge 84. The latch 72 swivels on the hinge 84 into the interlocking position illustrated. A cam means including a cam fixture 86 and a sliding cam 88 create the compressive force. When the rib 81 is properly positioned in the recess 82, the latch handle 74 is moved with the sliding cam 88 to engage the cam face 90 of the fixture 86 against the cam face 92 of the sliding cam 88. The action between the two cam faces 90 and 92 draws the latch 72 down trapping the rib 81 inside the recess 82.

FIG. 4b is a top plan view of the sliding cam 88 of FIG. 4a along the line 4b—4b. The sliding cam 88 contains a key hole 93 to direct the sliding cam action across the cam face 92.

Figure 5:
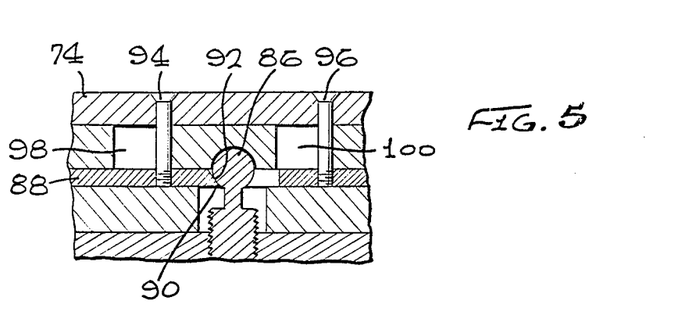
FIG. 5 is an enlarged sectional view along the line 5—5 of FIG. 1 through the longitudinal center of the door latch.

FIG. 5 is an enlarged sectional view along the line 5—5 of FIG. 1 of the cam fixture 86 rotated 90° from the view in FIG. 4. The latch handle 74 is connected to the sliding cam 88 by screws 94 and 96 that move in slots 98 and 100. As shown, the latch handle 74 is moved to the far right of the slots 98 and 100 forcing the cam face 92 of the sliding cam 88 under the cam face 90 of the fixture 86 trapping the rib 81 inside the recess 82.

Figure 6:
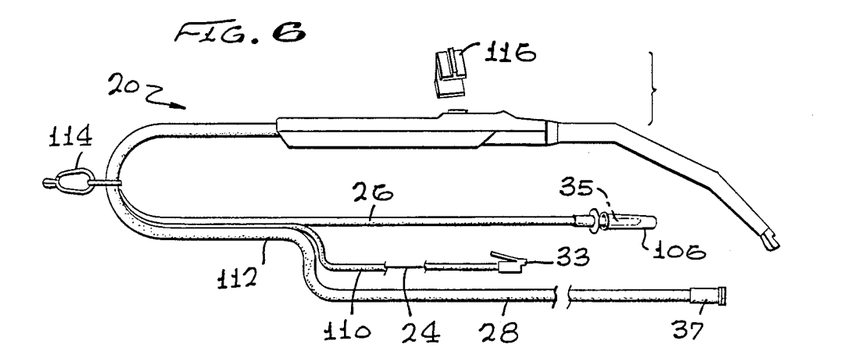
FIG. 6 is a perspective view of the surgical instrument.

FIG. 6 is a perspective view of the surgical instrument 20 separated from the support unit 22. The instrument 20 is easily and quickly attached to the support unit 22 by quick connectors at the ends of the tubing 26 and 28 and the electrical wiring 24. The wiring 24 has the modular telephone wiring connector 33 on its end. The flexible irrigation tube 26 has the standard hospital connector spike 35 on its end protected during storage by a cap 106. The flexible aspiration tube 28 has a standard hospital suction connector 37 designed to seal around the entrance to the container 38 (FIG. 1). The wiring 24 is preferably enclosed in a wiring tube 110 made of flexible electrically insulative material to provide further electrical protection. The diameter of the wiring tube 110 is selected to provide a loose fit between the wiring 24 and the tube allowing the wiring 24 to move longitudinally inside for maximum flexibility. The three tubes 26, 28, and 110 are extruded together forming a triple lumen tube 112 that is convenient to handle as a single unit. The tubes are easily separable from each other to meet the requirements of various operating room situations. A drape clip 114 permits the tube to be hung from a support. During storage of the instrument 20, an irrigation valve clip 116 is fitted over the handle member 32 to hold the valve open in order to prevent sticking as described more fully below in conjunction with FIG. 16.

Figures 7, 8, 9, 10, 11, 12, 13, 14, 15, 16, 17:
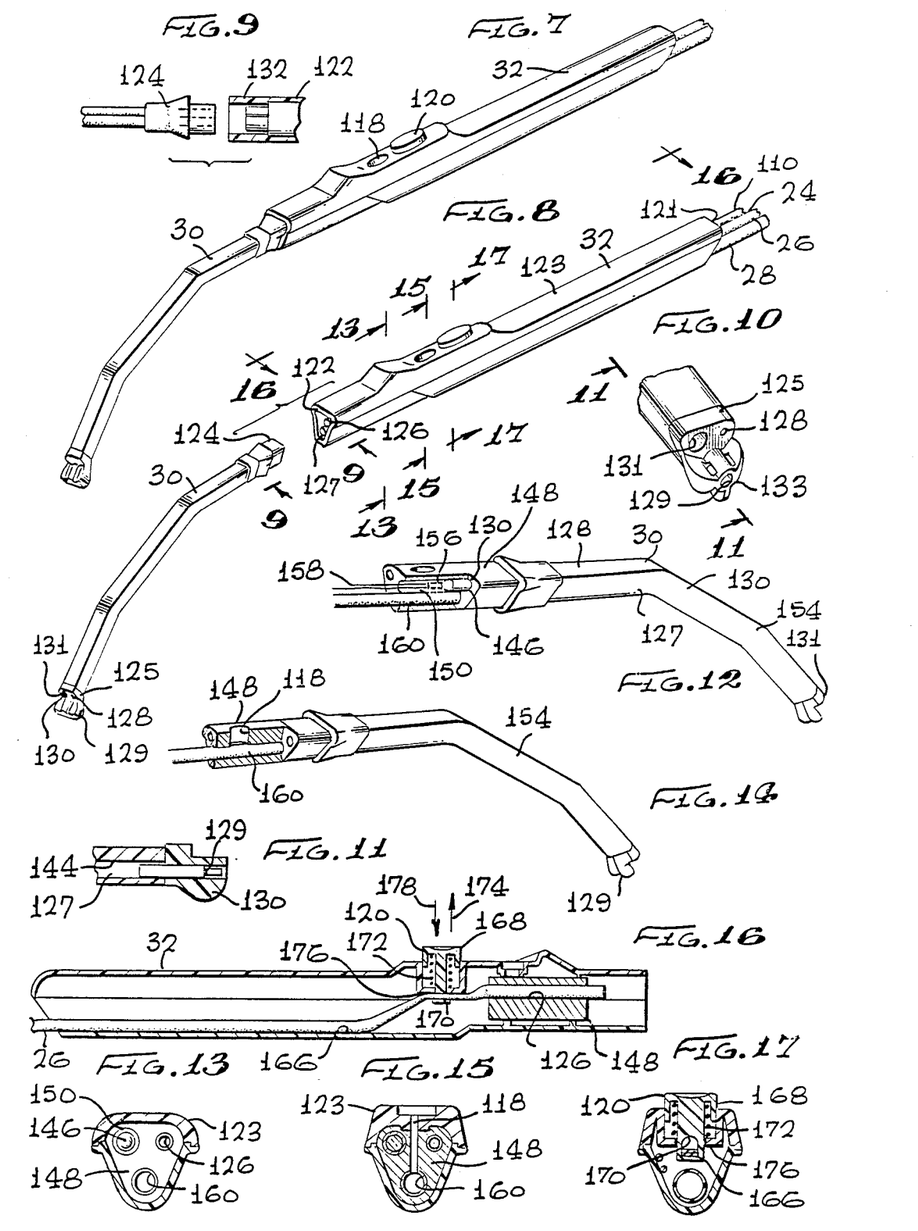
FIG. 7 is a perspective view of the probe and handle member.
FIG. 8 is a perspective view similar to FIG. 7 with the probe member detached.
FIG. 9 is a sectional view along the line 9—9 of FIG. 8 showing the probe and handle member connection.
FIG. 10 is an enlarged perspective view of the end of the probe member.
FIG. 11 is a sectional view along the line 11—11 of FIG. 10.
FIG. 12 is a longitudinal sectional view of the heat sink through the illumination passageway in relation to the probe member.
FIG. 13 is an enlarged sectional view along the line 13—13 of FIG. 8 through the lamp.
FIG. 14 is a longitudinal sectional view of the heat sink through the aspiration passageway in relation to a probe member.
FIG. 15 is an enlarged sectional view along the line 15—15 of FIG. 8 through the bleed hole.
FIG. 16 is a sectional view along the line 16—16 of FIG. 8 through the handle along the irrigation passageway in the heat sink.
FIG. 17 is an enlarged sectional view along the line 17—17 of FIG. 8 through the irrigation valve.

FIG. 7 is a perspective view of the probe and handle members 30 and 32. A bleed hole aperture 118 and an irrigation valve 120 respectively provide an aspiration control means and an irrigation control means. Both are located close to each other substantially along the longitudinal axis of the handle member 32 permitting the user to operate both simultaneously with a single finger. The irrigation valve 120 controls the flow of a first irrigation fluid through an irrigation passageway means in the probe and handle members 30 and 32. The bleed hole aperture 118 controls the flow of a second aspirated fluid through an aspiration passageway means in the probe and handle means 30 and 32.

FIG. 8 is a perspective view similar to FIG. 7 showing how the probe member 30 can be detached from the handle member 32. This optional feature allows probe members having different configurations to be utilized. The probe member 30 can be changed, for example, by pulling the probe member 30 from the handle member 32 and inserting a different probe member. The elongated handle member 32 has first and second ends 121 and 122 and a perimeter wall 123 defining a cross section dimensioned so as to fit comfortably in a user's one hand. The elongated probe member 30 has first and second ends 124 and 125 with the probe member first end 124 attachable to the handle member second end 122. An irrigation passageway means 126 and an aspiration passageway means 127 in the handle and probe members 32 and 30 extend from the handle member first end 121 to the probe member second end 125 terminating in an irrigation port 128 and an aspiration port 129, respectively. An illumination passageway means 130 in the probe member 30 extends from the probe member first end 124 to the probe member second end 125 terminating in an illumination port 131. The flexible irrigation tube 26 is connected to the irrigation passageway means 126 at the handle member first end 121. The flexible aspiration tube 28 is connected to the aspiration passageway means 127 also at the handle member first end 121. The electrical wiring 24 is connected to the lamp inside the handle member 32 and exits at the handle member first end 121. The electrical wiring tube 110 surrounds the wiring and terminates in the handle member 32.

FIG. 9 is a sectional view along the line 9—9 of FIG. 8 showing an exemplary probe member to handle member detachable connection. A sleeve 132 on the handle member second end 122 fits around and locks on the probe member first end 124. The tubes inside the handle member 32 fit inside tubes in the probe member 30.

FIG. 10 is an enlarged perspective view of the probe member second end 125 showing the irrigation port 128, the aspiration port 129, and the illumination port 131 all located at a small area at the probe member second end 125. In use, when aspiration is taking place, the aspiration port 129 is illuminated by light emanating from the illumination port 131. If irrigation is necessary for better viewing, debridement, or cleansing, the point where the irrigation occurs is lighted by light emanating from the illumination port 131. Aspiration of an expended irrigation fluid is immediate because the aspiration port 129 is automatically in the proper position.

FIG. 11 is a sectional view along the line 11—11 of FIG. 10. As show in FIGS. 10 and 11, the aspiration port 129 is surrounded and hidden by a cage 133 to minimize the potential for trauma to sensitive tissue and the total occlusion of the aspiration port 129 by keeping particles away that are larger than the port. The cage 133 provides several openings around the aspiration port 129. The aspiration passageway means 127 has a smaller cross sectional area at the aspiration port 129 than elsewhere along the interior indicated at 144 for keeping particles out of the aspiration passageway means 127 larger than the aspiration port 129. Openings in the cage 133 adjacent to the irrigation and illumination ports 128 and 131 tend to clear particles and fluids away from the ports 128 and 131.

FIG. 12 illustrates an electrically energizable lamp means 146, e.g. halogen for supplying high intensity light to the illumination passageway means 130 in the probe member 30. FIG. 12 is a longitudinal sectional view of a heat sink 148 taken through a passageway 150 extending through the heat sink 148. The heat sink 148 comprises a mass of highly heat conductive material and the lamp 146 is mounted in the passageway 150 so as to tightly thermally couple the lamp 146 to the heat sink 148. The probe member 30 is attached to the handle member in front of the heat sink 148 so that light from the lamp 146 is transmitted through the illumination passageway 130 to the illumination port 131 on the second end 125 of the probe member 30. The illumination passageway means 130 preferrably is an optical fiber (typically a bundle of fibers).

The halogen lamp 146 is selected to provide maximum optimal light when transmitted through the optical fiber and projected onto the incision. One of the prime purposes of the probe member 20 and the support unit 22 (FIG. 1) is to enchance the surgeon's ability to view the surgical cavity for improved diagnosis. Color is considered a key factor in diagnosing the quality of tissue. It is important to the performance of the probe member 20 that the color of the light emitted from the illumination port 131 be of a specific quality so as to not impart a yellow cast to the field of view. The use of a halogen lamp 146 mounted as close as possible to the illumination port 131 and the use of a high transmissivity rigid glass fiber yields optimal results. Since a glass optical fiber is fragile, the aspiration passageway means 127 is preferably fabricated of rigid material, e.g. stainless steel, to act as a brace for protecting the fiber from stresses. A protective sleeve 154 is positioned around the optic fiber and the aspiration and illumination passageway means 128 and 130 on the probe member 30 to retain portions of the optical fiber in case of breakage. Only a portion of the sleeve 154 is shown in FIG. 12. The entire sleeve 154 is shown in FIG. 14.

The use of a high intensity halogen lamp 146 delivering approximately 500-3000 foot candles creates the potential for heat problems. The lamp 146 generates approximately 8 watts of heat during use. In an uncontrolled condition this power could develop temperatures within the handle member 32 in excess of 300° F. Temperatures must be monitored and controlled for proper and safe use to avoid transferring uncomfortable amounts of heat to the user's hand. A heat sensing means in the form of a thermistor 156 is provided for sensing the temperature level of the handle member 32 (FIG. 8) and providing a probe temperature signal through a lead 158 to the support unit 22. As will be discussed, the support unit 22 includes a microprocessor for reducing or turning off the electrical power to the lamp 146 if the temperature gets too high. In normal operation, the aspirated fluid flows continuously through the aspiration passageway means 127 from the aspiration port 129 illustrated in FIG. 10. This fluid flow is utilized to dissipate the heat generated by the lamp 146. More specifically, the heat sink 148 thermally couples the lamp 146 with the second fluid in the aspiration passageway means 127 by including a tubular section 160 of the aspiration passageway means 127 through the heat sink 148. The tubular section 160 enables the second fluid to convey heat away from the heat sink mass.

FIG. 13 is an enlarged sectional view along the line 13—13 of FIG. 8 through the lamp 146 showing the relationship in the heat sink 148 between the lamp 146 and the aspiration passageway tubular section 160. Also passing through the heat sink 148 parallel to the lamp passageway 150 and the aspiration passageway tubular section 160 is the irrigation passageway means 126. The perimeter wall 123 insulates the user's hand from the heat sink 148.

FIG. 14 is a longitudinal sectional view of the heat sink 148 through the aspiration passageway tubular section 160. The bleed hole aperture 118 is incorporated into the heat sink 148 to provide additional surface area for cooling the heat sink 148. FIG. 15 is an enlarged sectional view along the line 15—15 of FIG. 8 through the bleed hole aperture 118 showing the cooling area provided by the bleed hole aperture 118. The bleed hole aperture 118 extends through the perimeter wall 123 and the heat sink 148 to communicate with the aspiration passageway tubular section 160. During operation, aspiration fluid is sucked into the aspiration port 129 and air is sucked into the bleed hole 118 (FIG. 10). The suction action at the aspiration port 129 can be controlled by the user using his finger to vary the covering of the bleed hole 118.

FIG. 16 is a sectional view along the line 16—16 of FIG. 8 through the handle member 32 along the irrigation passageway means 126 where it passes through the heat sink 148. The first irrigation fluid flowing through the irrigation passageway means 126 can thereby also convey heat away from the heat sink 148.

The irrigation passageway means 126 also includes a compliant portion 166. When the compliant portion 166 is collapsed by the valve 120, no irrigation fluid passes through the irrigation passageway means 126. When the compliant portion 166 is open, the irrigation fluid passes through the irrigation passageway means 126. The valve 120 has a plunger 168 mounted in the handle member 32 for reciprocal movement perpendicular to the elongation of the handle means 32. The plunger 168 has a tube aperture 170 through which the compliant portion 166 passes. A biasing means, e.g. a coiled spring 172, moves the plunger 168 in a first direction indicated by the arrow 174 normally collapsing the compliant portion 166 against a shoulder 176 surrounding the plunger 168 to close the irrigation passageway means 126 to the flow of the first irrigation fluid. When the plunger 168 is selectively moved by a finger in a second direction indicated by the arrow 178, the compliant portion 166 is moved away from the shoulder 176 allowing the first irrigation fluid to pass through the irrigation passageway means 126. To prevent sticking of the compliant portion 166 when the surgical instrument 20 is placed into service, it is preferable that a retainer clip 116 (FIG. 6) be provided to hold the plunger 168 down when the instrument is stored, i.e. during shelf life.

FIG. 17 is an enlarged sectional view along the line 17—17 of FIG. 8 through the irrigation valve 120. The spring 172 acting on the plunger 168 causes the collapsing of the compliant portion 166 between the side of the aperture 170 and the shoulder 176.

Figure 18:
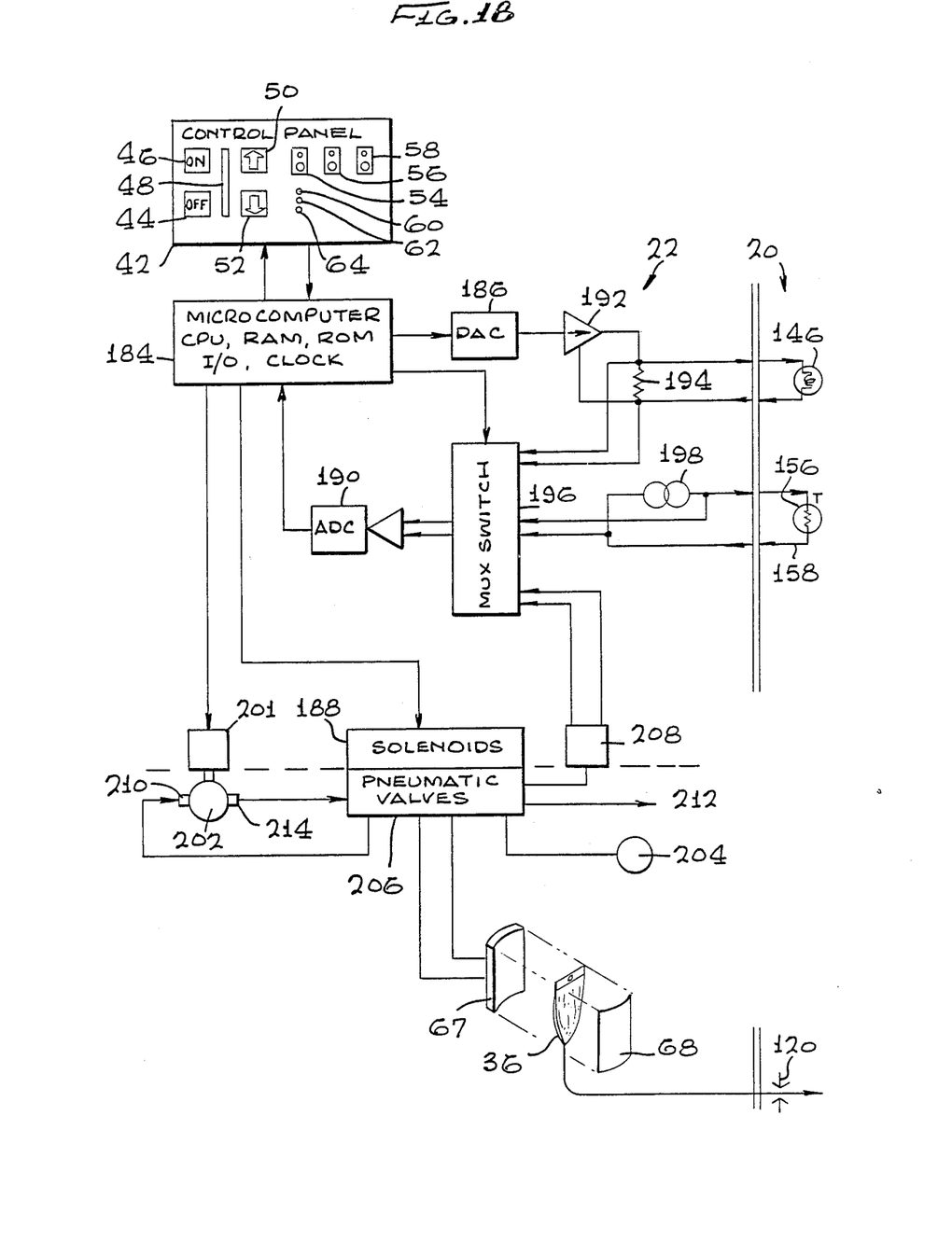
FIG. 18 is a block diagram of the electronic and pneumatic systems in accordance with the present invention.

FIG. 18 is a block diagram of the electronic and pneumatic systems of both the surgical instrument 20 and the support unit 22 in accordance with the present invention. The instrument 20 is represented to the right of the vertical double line and the support unit 22 is represented to the left. The electronic portions of both are represented above the horizontal dashed line and the pneumatic portions are represented below. The support unit 22 provides a control means for the functions of the surgical instrument 20 and has four major subsystems: the control panel 42, a logic system, an illumination system, and a pneumatic system.

The control panel 42 provides an interface between the operator of the support apparatus 22 and the logic system. The control panel 42 has the "irrigation off" switch 44, the "irrigation on" switch 46, the current and set point irrigation pressure bar graph 48, the "pressure increase" switch 50, the "pressure decrease" switch 52, the "lamp off" switch 54, the "lamp on low" switch 56, the "lamp on high" switch 58, the "lamp operating properly" indicator 60, the "aspiration blockage" indicator 62, and the "lamp defective" indicator 64.

A microcomputer 184 is the heart of the logic system and includes a read only memory (ROM) for storing a predetermined set of instructions for controlling a central processing unit (CPU). Parameter data is stored in a random access memory (RAM). A clock generator is provided for circuit timing and input/output circuitry is provided for interfacing. The other electronic components include the control panel 42, a digital to analog converter (DAC) 186 for controlling lamp energization, solenoids 188 for controlling pneumatic control valves, and an analog to digital converter (ADC) 190 for supplying parameter data to the CPU.

The illumination system provides an electrical supply means for the probe lamp 146 and is controlled by depressing one of the lamp control switches 54, 56, or 58 on the control panel 42. The lamp control switches 54, 56, and 58 provide a means for adjusting the intensity of the lamp 146 and are read by the microcomputer 184 to provide a lamp intensity value which is supplied to the DAC 186. The resulting output of the DAC 186 controls a current source 192 and thus the current supplied to the lamp 146. The resulting voltage measured across the lamp 146 (i.e., a resistor 194) is fed into one of the input channels of a multiplexer switch (MUX switch) 196. The thermistor 156 in the handle member 32 of the instrument 20 provides another input to the MUX switch 196. A constant current source 198 supplies a voltage to the thermistor that is modified by the resistance of the thermistor. The thermistor 156 changes resistance in relation to its temperature and thus the voltage across the thermistor 156 comprises a probe temperature signal. This voltage is fed into another channel of the MUX switch 196. The microcomputer 184 increments through each channel of the MUX switch 196 and inputs the parameter data voltages into the ADC 190 where they are converted into digital values. The microcomputer 184 then stores these lamp and temperature voltages into the RAM and makes a series of decisions to control the lamp 146 and various indicator lamps on the control panel 42.

When the lamp and thermistor voltages are within acceptable limits, the "lamp operating properly" indicator 60 is activated and the lamp current (i.e., output of a lamp current source 192) is maintained at the established level. If the lamp voltage is above its limit indicating an open circuit, below its limit indicating a short circuit, or the thermistor voltage is above its limit indicating an open circuit, the "lamp defective" indicator 64 is activated and the lamp current is turned off. When the thermistor voltage is below its limit indicating unacceptably high temperatures in the handle 32, the "aspiration blockage" indicator 62 is activated indicating a blockage of the passageway of the surgical instrument 20 and the lamp current is reduced or turned off. The "light operating properly" indicator 60 and the "light defective" indicator 64 provide further information to the operator of the support apparatus 22 for determining the exact nature of a problem if one occurs. When the thermistor voltage returns to an acceptable limit, the electric power provided by the lamp current source 192 is returned to its previous level.

The irrigation system provides a source of pressurized irrigation fluid to the surgical instrument 20. The irrigation system includes the bladder 67 located in the back of the chamber 66 illustrated in FIG. 1. The flexible bag 36 is enclosed in the chamber 66 between the bladder 67 and the door 68. When the bladder 67 is pressurized and expands against the flexible bag 36, the bag 36 is pressed against the door 68 creating pressure inside the bag 36. The operator of the instrument 20 is then able to dispense irrigation fluid by means of the irrigation valve 120. Pressure to the irrigation fluid is maintained during use by increasing the volume of the bladder 67.

When pressurization is begun by pushing the "irrigation on" switch 46, the microcomputer sends electrical power to a pump motor 201 starting an air pump 202. The microcomputer 184 then activates the solenoids 188 to set the pneumatic valves 206 to supply air to the bladder 67. A pressure transducer means 208 measures the pressure in the bladder 67 and provides a bladder pressure level signal. The microcomputer 184 continually registers the digital representation of the bladder pressure level signal through the MUX switch 196 and ADC 190 and maintains the solenoids 188 in the present position until the bladder pressure reaches the pressure set point. Modification of the set point pressure may be made as desired by depressing either the "irrigation pressure increase" switch 50 or the "irrigation pressure decrease" switch 52. The irrigation pressure set point is indicated by a bright bar on the pressure bar graph 48. The actual pressure in the bladder 67 as measured by the pressure transducer 208 is reflected on the bar graph 48 by a medium lit bar. The pump 202 continues to pressurize the bladder 67 until the bladder pressure set point is reached at which time the microcomputer 184 isolates the bladder 67 from the pump 202 and the pressure transducer 208 by changing the position of the solenoids 188.

The pump 202 also acts to pressurize an accumulator 204. The pressure transducer 208 is now set to provide an accumulator pressure level signal. When the set point for the accumulator maximum pressure is reached, the microcomputer 184 stops the motor 203 and sets the solenoids 188 to allow the pressure transducer 208 to measure the bladder pressure level again. When air is again needed by the bladder 67 to maintain the desired bladder pressure level, the microcomputer 184 bleeds air from the accumulator 204 to the bladder 67. When bladder pressure can no longer be maintained by bleeding air from the accumulator 204, the microcomputer 184 again starts the pump motor 203 starting the pressurization process again.

When the irrigation pressure off switch 44 is pressed, the support unit 22 evacuates the bladder 67 in order to permit rapid changing of the used irrigation bag 36 for a new one. The microprocessor 184 begins the process by starting the pump motor 203 and changing the solenoids 188 to connect the vacuum side 210 of the pump 202 to the bladder 67 and opening a pressure vent valve 212 on the pressure side 214 of the pump 202 to vent the pressurized air to the atmosphere. The pump 202 continues until the bladder 67 is empty.

Figure 19:
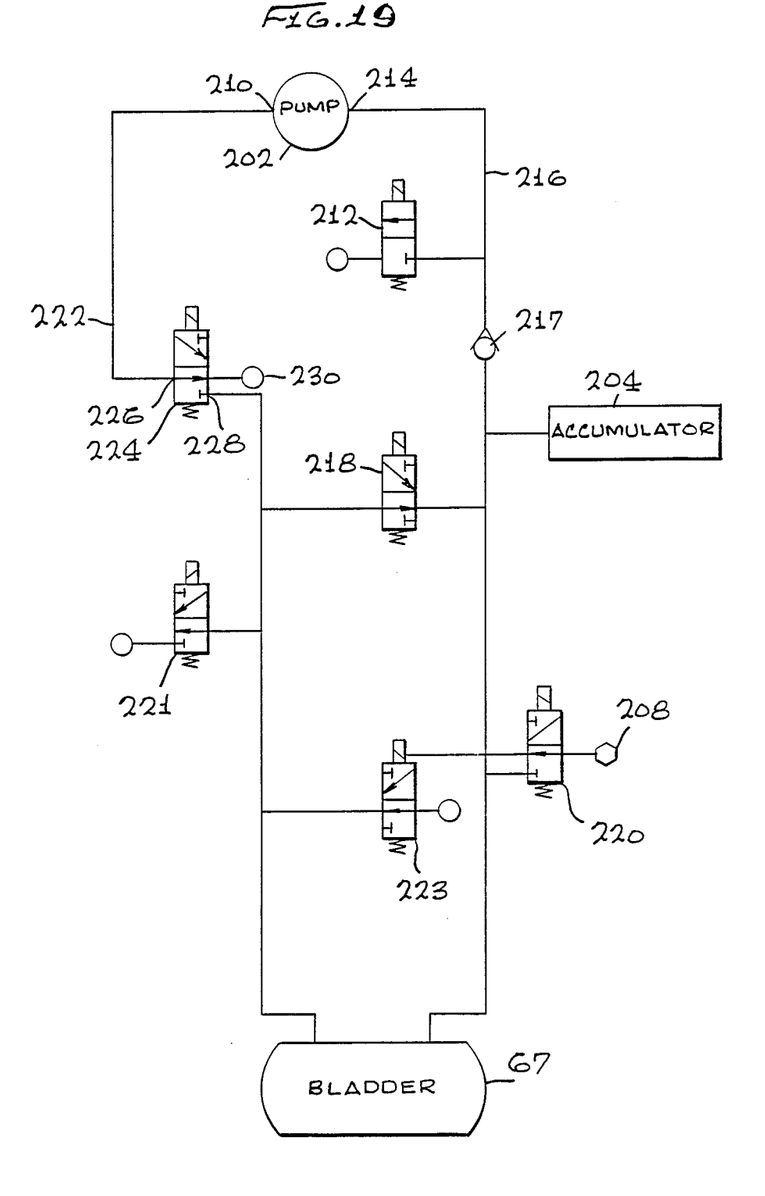
FIG. 19 is a diagram of the pneumatic circuit in accordance with the present invention.

FIG. 19 is a diagram of the pneumatic circuit in accordance with the present invention. The previously described elements include the pump 202, the pressure vent valve 212, the accumulator 204, the pressure transducer 208, and the bladder 67. A first conduit 216 connects between the pressure side 214 of the pump 202 and the bladder 67. A check valve 217 is provided between the pump 202 and the accumulator 204 to prevent reverse flow of air. A bladder isolation valve 218 in the conduit 216 isolates the bladder 67 from the accumulator 204 when the bladder 67 is inflated and the pump 202 continues to pressurize the accumulator 204. The bladder isolation valve 218 is also utilized to bleed air from the accumulator 204 to the bladder 67 when the pump 202 is not operating. A transducer valve 220 permits the use of a single transducer 208 to measure the pressure in both the bladder 67 and the accumulator 208. A slow vent valve 221 is provided to bleed pressure from the bladder 67 when it exceeds the set point. A second conduit 222 connects the vacuum side 210 of the pump 202 and the bladder 67 to provide a means for evacuating the bladder 67. A system vent valve 223 is provided to release the pressure in the bladder 67 when the "irrigation off" switch 44 is depressed. A vacuum vent valve 224 in the second conduit 222 is connected to the pump 202 through an outlet port 226. The pump 202 deflates the bladder 67 when the valve 224 is set to a first inlet port 228 leading to the bladder 67. When the valve 224 is set to a second inlet port 230 open to the atmosphere, the pump 202 is able to again pressurize the bladder 67.

Figure 20:
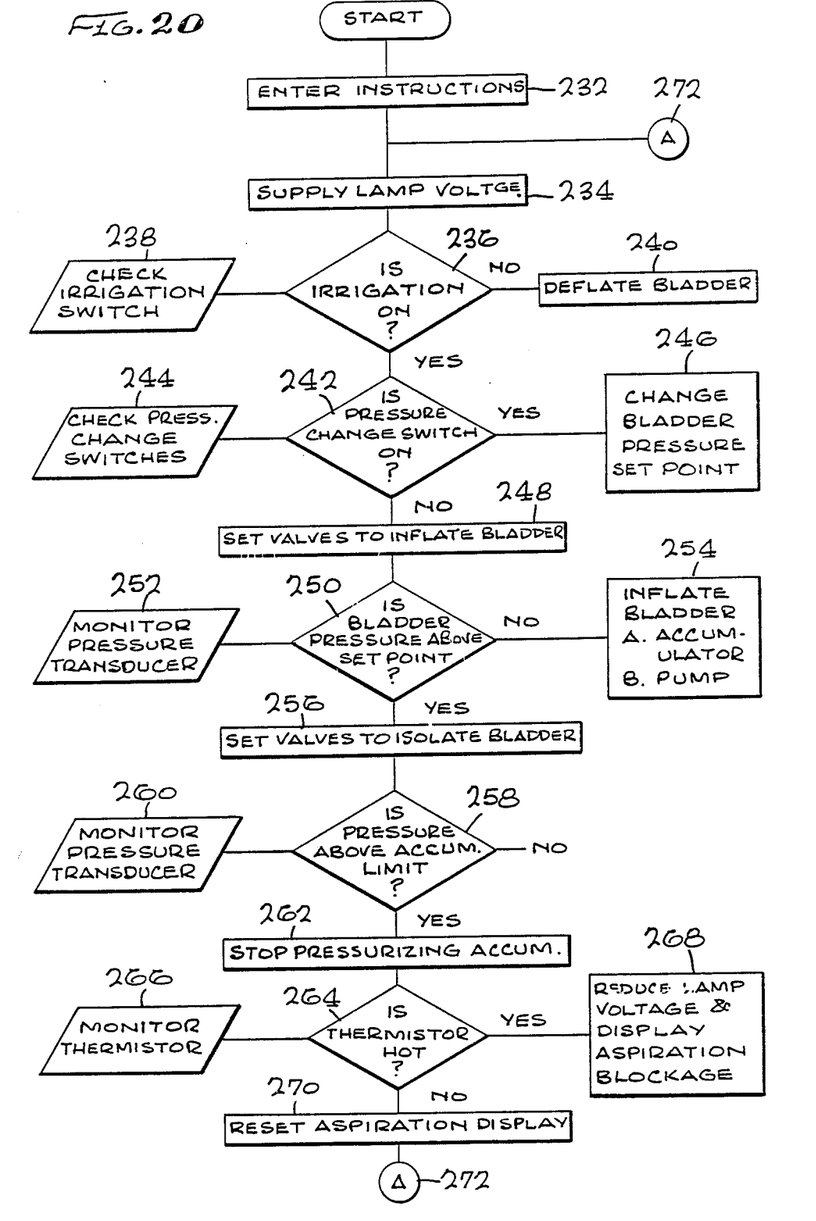
FIG. 20 is a flow chart depicting a signal processing methodology and structure in accordance with the principles of the present invention.

FIG. 20 is a flow chart depicting an exemplary signal processing methodology and structure in accordance with the principles of the present invention. The operation is initiated by the entry of a predetermined set of instructions from the ROM into the CPU (input block 232). The microcomputer 184 then instructs the lamp current source 192 to supply current to the lamp 146 (process block 234).

The first test performed is to determine if the irrigation pressure switch 46 is on (test block 236). The switch 46 is checked (input block 238) and if the switch 46 is on the process continues to the next test. If the switch 46 is not on, the deflate bladder sequence is initiated (process block 240) as described above in conjunction with FIGS. 18 and 19. The deflate bladder sequence does not occur when the bladder 67 has never been inflated.

The second test determines if an irrigation pressure change switch 50 or 52 is activated (test block 242) by checking the pressure change switches (input block 244) and changes the bladder pressure set point (process block 246) if a change is being made. A means is thereby established for achieving a desired bladder pressure set point. If no change is being made, the default value is utilized to establish the set point. If a change has been made, the new value is utilized to establish the set point. The microprocessor 184 then sets the solenoid valves 206 to inflate the bladder 67 (process block 248).

Prior to initiating the bladder pressurization, another test is performed to determine if the bladder pressure is already above the bladder pressure set point (test block 250). The microcomputer 184 monitors the pressure transducer 208 (input block 252). If the bladder 67 is not above the set point, the bladder 67 is inflated to the set point either by bleeding air from the accumulator 204 or by operation of the pump 202. If the bladder 67 is above the pressure set point, the solenoid valves 206 are set to isolate the bladder 67 (process block 256) and continues the pressurization of the accumulator 208 if the pump 202 is operating.

The next test determines if the pressure in the accumulator 204 is above the accumulator pressure limit determined by the predetermined set of instructions (test block 258). The tranducer 208 is switched to measure the pressure in the accumulator 204 and the resulting signal is monitored by the microprocessor (input block 260). If the pressure is not above the accumulator pressure limit, the pump 202 continues operating. If the pressure is above the pressure limit, the pump 202 stops pressurizing the accumulator 208 (process block 262).

The last test determines if the thermistor 156 is too hot (test block 264). The thermistor is monitored (input block 266) and if it is too hot, the lamp voltage provided by the lamp current source 192 is reduced or discontinued (process block 268) and the aspiration blockage indicator 62 is activated. If the thermistor temperature is not too hot or when the temperature returns to a satisfactory level, the aspiration blockage indicator 62 is reset (process block 270).

When the last operation is completed, the program loops back (loop 272) to start the entire process over. It should be noted that the microcomputer 184 continuously cycles through the program illustrated in FIG. 20 and does not wait for a particular function to be completed such as the pressurization of the bladder 67 (process block 254) before going on to the next step.

In view of the above, it may be seen that a surgical instrument and cooperating support unit are provided for illuminating, irrigating, and aspirating a surgical incision. Significant improvements in operating procedures are thereby achieved. Of course, the structure may be variously implemented and variously used depending upon specific applications. Accordingly, the scope hereof shall not be referenced to the disclosed embodiment, but on the contrary, shall be determined in accordance with the claims as set forth below.

We claim:

1. A surgical instrument for enabling a user using one hand to probe an incision and illuminate, irrigate and aspirate said incision, said instrument comprising:
   an elongated handle member having first and second ends and a perimeter wall defining a cross section dimensioned so as to fit comfortably in said user's one hand;
   an elongated probe member having first and second ends, said probe member first end attached to said handle member second end;
   irrigation passageway means in said handle member and probe member extending from said handle member first end to said probe member second end for conveying a first fluid from a fluid supply coupled to said handle member first end for discharge at said probe member second end;
   aspiration passageway means in said handle member and probe member extending from said handle member first end to said probe member second end for drawing a second fluid from said probe member second end to a vacuum source coupled to said handle member first end;
   illumination passageway means in said probe member for conducting light from said probe member first end to said probe member second end;
   electrically energizable lamp means for supplying light proximate to said illumination passageway means at said probe member first end;
   a heat sink comprising a mass of highly heat conductive material tightly thermally coupled to said lamp means and having a tubular section extending therethrough for enabling said second fluid to pass therein to convey heat away from said heat sink mass; and wherein
   said aspiration passageway means includes said tubular section. said heat sink mass.

2. The instrument of claim 1 further including an aspiration control means operable to control the flow of said second fluid through said aspiration passageway means.

3. The instrument of claim 2 wherein said perimeter wall insulates said user's one hand from said heat sink mass and said aspiration control means includes a bleed hole aperture extending through said perimeter wall and said heat sink mass and communicating with said aspiration passageway tubular section.

4. The instrument of claim 1 wherein said lamp means is mounted within said peripheral wall of said handle member.

5. The instrument of claim 1 wherein said handle member further includes an electronic heat sensing means providing a probe temperature signal for sensing the temperature level of said handle member.

6. The instrument of claim 1 further including a flexible irrigation tube connected to said irrigation passageway means at said handle member first end and a flexible aspiration tube connected to said aspiration passageway means at said handle member first end.

7. The instrument of claim 6 further including electrical wiring connected to said lamp means and exiting from said handle member at said handle member first end; and
   a tube of flexible electrically insulative material enclosing said wiring.

8. The instrument according to claim 1 further including means for detachably attaching said probe member first end to said handle member second end.

9. The instrument according to claim 1 wherein said second end of said probe member includes an aspiration port at the end of said aspiration passageway means and a cage surrounding said aspiration port for preventing particles from blocking said aspiration port.

10. The instrument according to claim 1 wherein said illumination passageway means includes a rigid optical fiber and said probe member further include a rigid brace for protecting said fiber from stresses.

11. The instrument of claim 2 including an irrigation control means operable to control the flow of said first fluid through said irrigation passageway; and wherein said aspiration and irrigation control means are mounted on said handle member in close proximity to one another permitting the user to simultaneously operate both said aspiration and irrigation control means with a single finger.

12. The instrument of claim 11 wherein said irrigation passageway means includes a compliant portion and wherein said irrigation control means comprises:
   a plunger mounted in said handle means for reciprocal movement perpendicular to the elongation thereof, said plunger including an aperture for passing said compliant portion therethrough; and
   a biasing means for moving said plunger in a first direction against said compliant portion for normally closing said irrigation passageway means to the flow of said first fluid;
   whereby the plunger can be selectively moved in a second direction for permitting said first fluid to pass through said irrigation passageway means.

13. The instrument according to claim 12 wherein said aspiration passageway means has a smaller cross sectional area at said aspiration port than elsewhere for keeping particles out of said aspiration passageway means larger than said aspiration port while freely transporting particles inside said aspiration passageway means.

14. The instrument according to claim 12 wherein said irrigation passageway means, said aspiration passageway means, and said illumination passageway means respectively terminate at an irrigation port, an aspiration port, and an illumination port at said probe member second end; and wherein
   said cage includes openings for drawing particles away from said irrigation port and said illumination port.

15. The instrument according to claim 10 wherein said probe member further includes a protective sleeve around said optical fiber to retain portions of said fiber in case of breakage.

16. The instrument according to claim 10 wherein said rigid brace comprises a rigid tube forming part of said aspiration passageway means.

17. A surgical instrument for enabling a user using one hand to probe an incision and illuminate and aspirate said incision, said instrument comprising:
   an elongated handle member having first and second ends and a perimeter wall defining a cross section dimensioned so as to fit comfortably in said user's one hand;

an elongated probe member having first and second ends, said probe member first end attached to said handle member second end;

aspiration passageway means in said handle member and probe member extending from said handle member first end to said probe member second end for drawing a fluid from said probe member second end to a vacuum source coupled to said handle member first end;

illumination passageway means in said probe member for conducting light from said probe member first end to said probe member second end;

electrically energizable lamp means for supplying light proximate to said illumination passageway means at said probe member first end;

a heat sink comprising a mass of hightly heat conductive material tightly thermally coupled to said lamp means and having a tubular section extending therethrough for enabling said fluid to pass therein to convey heat away from said heat sink mass; and wherein said aspiration passageway means includes said tubular section.

18. The instrument of claim 17 further including an aspiration control means operable to control the flow of said fluid through said aspiration passageway means.

19. The instrument of claim 18 wherein said perimeter wall insulates said user's one hand from said heat sink mass and said aspiration control means includes a bleed hole aperture extending through said perimeter wall and said heat sink mass and communicating with said aspiration passageway tubular section.

20. The instrument of claim 17 wherein said lamp means is mounted within said peripheral wall of said handle member.

21. The instrument of claim 17 wherein said handle member further includes heat sensing means for sensing the temperature level of said handle member.

22. The instrument according to claim 17 further including means for detachably attaching said probe member first end to said handle member second end.

23. The instrument according to claim 17 wherein said second end of said probe member includes an aspiration port at the end of said aspiration passageway means and a cage surrounding said aspiration port for preventing particles from blocking said aspiration port.

* * * * *